United States Patent [19]
Matyas et al.

[11] Patent Number: 5,866,417
[45] Date of Patent: Feb. 2, 1999

[54] METHOD OF TISSUE TRANSFER

[76] Inventors: John R. Matyas, 1606 21 Ave., N.W., Calgary, Alberta, Canada, T2M 1M1; Jerome B. Rattner, 35 P-1 McKay Ct., Calgary Alberta, Canada, T3B 5B7

[21] Appl. No.: 550,629

[22] Filed: Oct. 31, 1995

Related U.S. Application Data

[63] Continuation-in-part of Ser. No. 438,956, May 11, 1995, which is a continuation-in-part of Ser. No. 242,290, May 13, 1994, abandoned.

[51] Int. Cl.$^6$ ........................................... C12N 5/06
[52] U.S. Cl. ................................. 435/378; 435/174
[58] Field of Search ............................... 435/174, 240.2, 435/240.21, 240.23, 240.241, 378

[56] References Cited

U.S. PATENT DOCUMENTS

| | | | |
|---|---|---|---|
| 2,591,927 | 4/1952 | Gladstone | 128/2 |
| 2,601,513 | 6/1952 | Gladstone | 128/2 |
| 4,508,819 | 4/1985 | Rose | 435/1 |
| 4,627,836 | 12/1986 | MacGregor | 604/93 |
| 4,670,286 | 6/1987 | Nyilas et al. | 427/2 |
| 4,996,154 | 2/1991 | Gabriels, Jr. | 435/240.241 |
| 5,229,045 | 7/1993 | Soldani | 264/41 |
| 5,282,851 | 2/1994 | Jacob-LaBarre | 623/6 |
| 5,374,515 | 12/1994 | Parenteau et al. | 435/1 |
| 5,489,306 | 2/1996 | Gorski | 623/16 |
| 5,510,254 | 4/1996 | Naughton et al. | 435/240.243 |

FOREIGN PATENT DOCUMENTS

| | | |
|---|---|---|
| 2506017 | 11/1982 | France . |
| WO 93/04193 | 3/1993 | WIPO . |

OTHER PUBLICATIONS

Hirono, J. et al., "Simultaneous recording of [Ca$^{2+}$]$_I$ increases in isolated olfactory receptor neurons retaining their original spatial relationship in intact tissue", J. Neurosci. Meth. 42:185–194, 1992.

Schleicher & Schuell, "Product Guide & Methods", pp. 5–19, 1992.

Taylor, R. et al., Tissue Printingas a Tool for Observing Immunological and Protein Profiles in Young and Mature Celery Petioles, Plant Physiol. (1993) 102: pp. 1027, 1029, 1031.

Mostbeck, G.H. et al., "Optimal Needle Size For Renal Biopsy: In Vitro and In Vivo Evaluation", Radiology, vol. 173, 1989, pp. 819–822.

Benediktsson H. et al., Enhanced Clomerular Retrieval In Renal Biopsies:, Clinical & Investigative Medicine (Annual Meeting of the Canadian Society for Clinical Investigation, Toronto, Sep. 1994, abstract.

Leet, N.G. et al., Rapid Method For Processing Entire Biopsy Pieces For Light And Electron Microscopy, Laboratory Practice, vol. 23, No. 2, Feb. 1974, pp. 59–60.

Dubenshy, T. et al., "Detection of DNA and RNA virus genomes in organ systems of whole mice", J. Virol. 50:779–783, 1984.

Reid, P. et al., "Tissue Printing, Tools for the study of Anatomy, Histochemistry, and Gene Expression", Acad. Press, Chapter 9 pp. 139–151, 1992.

Taylor, R. et al., Tissue Printing as a Tool for Observing Immunological and Protein Profiles in Young and Mature Celery Petioles, Plant Physiol. (1993) 102: 1027, 1029, 1031.

*Primary Examiner*—Jean C. Witz
*Attorney, Agent, or Firm*—Brown, Pinnisi & Michaels, PC

[57] ABSTRACT

The Tissue Transfer method consists of transferring intact, organized cells from the surfaces of biological tissues or organs to a transfer substrate. A surface of the tissue or organ is selected, in most cases, a freshly cut surface. At least one layer of intact cells is transferred by adhesion of the cells to a transfer substrate, which is a membrane, film, plate or liquid layer bound to a solid structure. The substrate is brought into contact with the selected surface and removed. A layer of cells is removed by the adhesion of the cells to the substrate and the cells retain the organization of the organ or tissue.

3 Claims, 6 Drawing Sheets

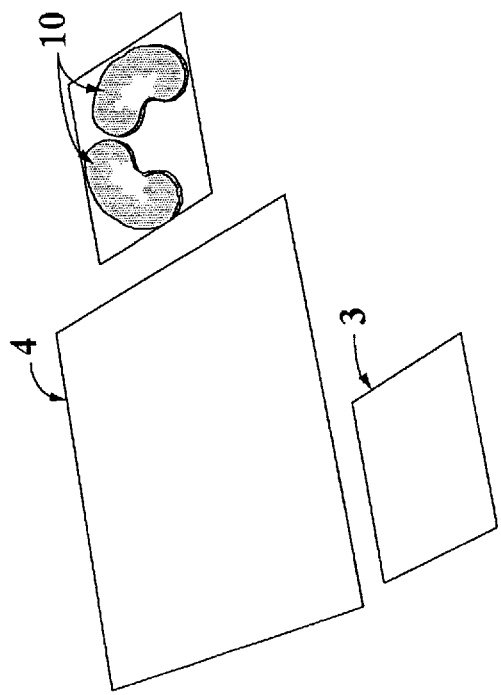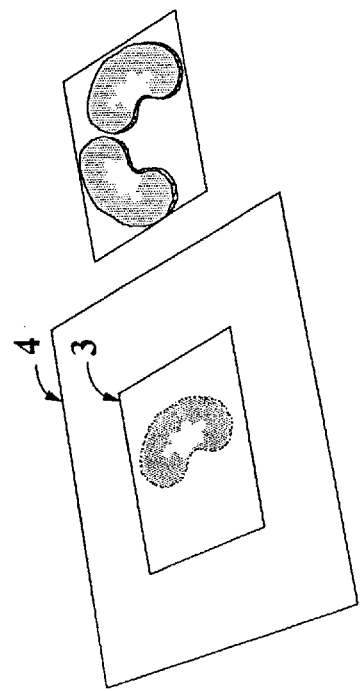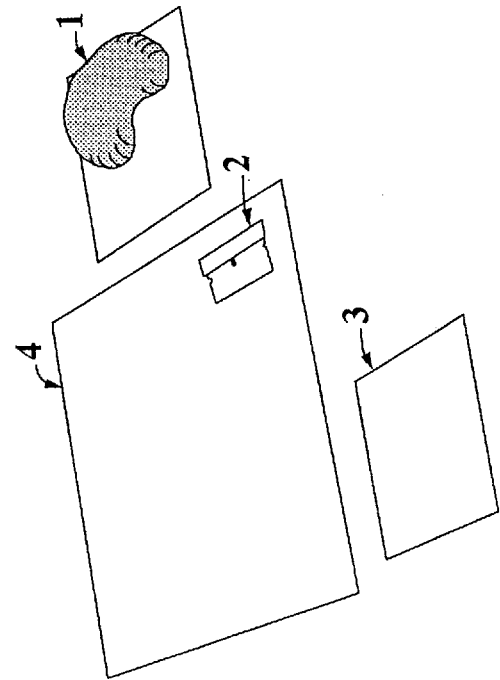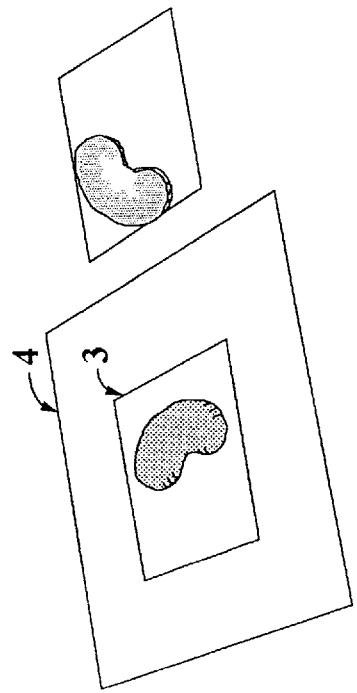
FIG 1a
FIG 1b
FIG 1c
FIG 1d

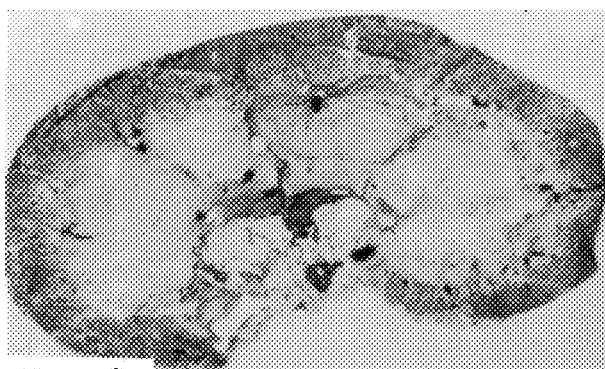
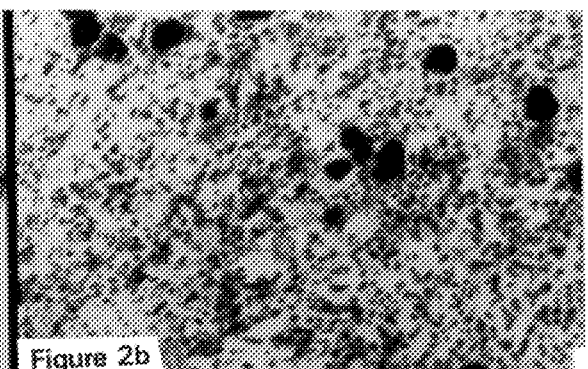
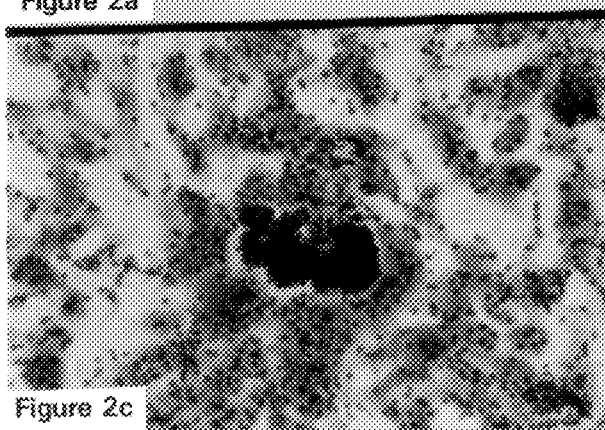
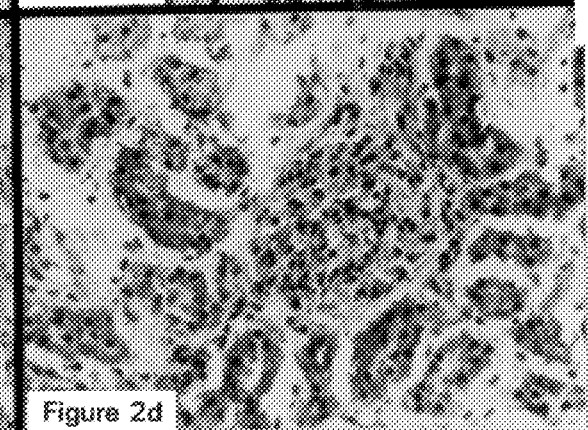

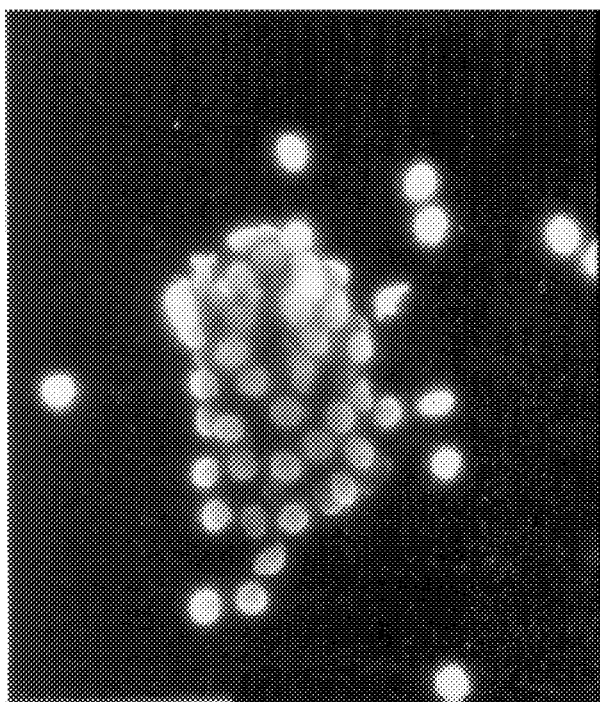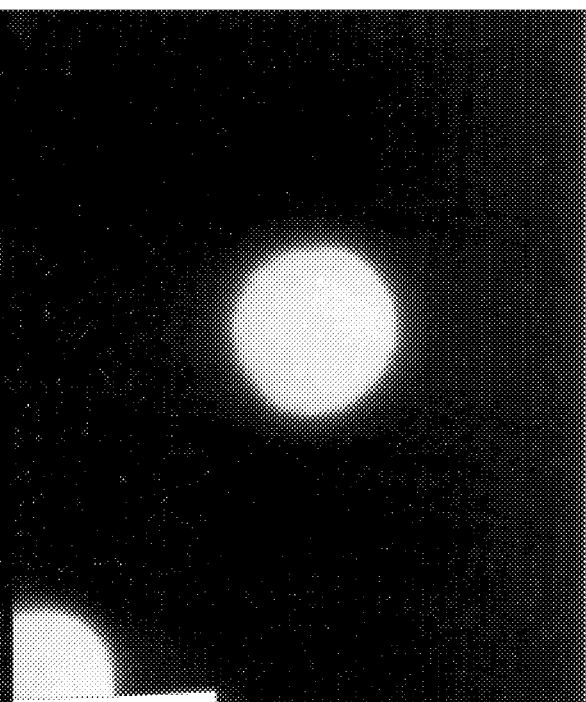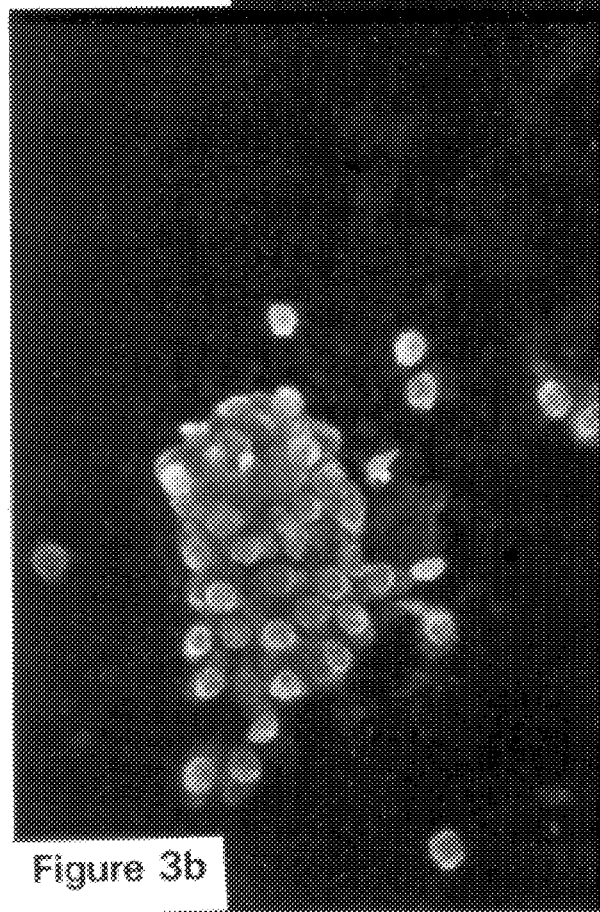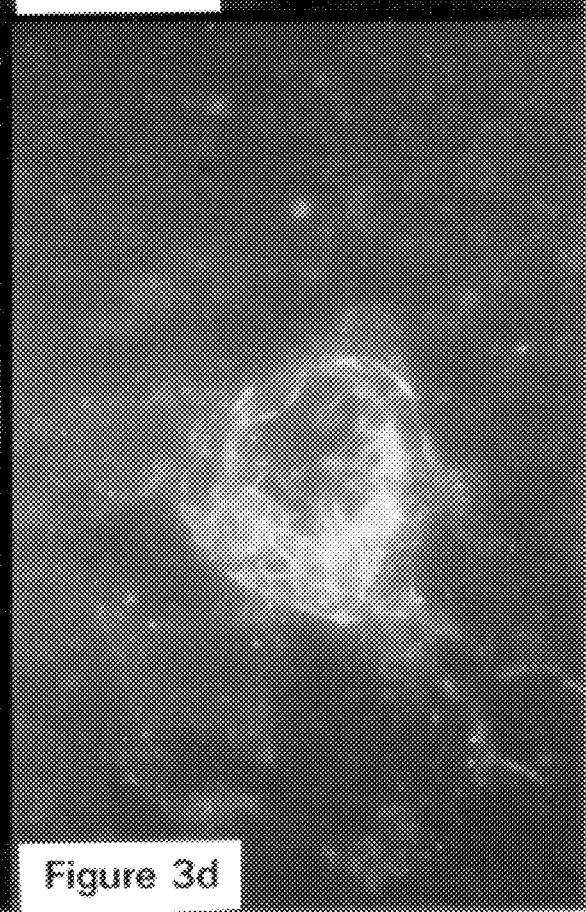

METHOD OF TISSUE TRANSFER

CROSS REFERENCE TO RELATED APPLICATIONS

This is a continuation-in-part application of co-pending application Ser. No. 08/438,956, filed May 11, 1995 entitled "METHOD OF TISSUE TRANSFER AND RETRIEVAL" which is a continuation-in-part application of application Ser. No. 08/242,290, filed May 13, 1994 entitled "METHOD OF TISSUE TRANSFER," now abandoned.

FIELD OF THE INVENTION

The invention pertains to the field of histology. More particularly, the invention pertains to the transfer of a layer of cells from tissue or an organ to a membrane such that the cells retain tissue or organ architecture and organization and a method of retrieving tissue during a renal biopsy.

BACKGROUND OF THE INVENTION

Organs and tissues are sampled by medical researchers and clinical physicians to better understand the anatomy and physiology of their patients. These samples are used to assess the structure and function of the organ in vivo.

The structure and function of an organ depends on the structure and function of its constituent cells and on the spatial relationships among cells of various types. Cells of common embryological origin that perform a common function are defined as tissues, which come in four basic types: muscle, nerve, epithelium, and connective tissues. As each cell type has a specific metabolism, it follows that each tissue has a characteristic function. An organ is a collection of different tissues combined in various proportions and patterns such that each organ has a characteristic, three-dimensional architectural structure. This complex architecture endows an organ with unique and complex functions that are more than simply the additive metabolism of its tissue and cellular components.

Each organ is an example of a complex arrangement of tissues acting in synergy to produce a complex function. The heart, for instance, is an organ formed primarily of muscle tissue that cannot function properly without its connective tissue "skeleton" that supports the muscle and forms the valves. Another example is kidney, where a complex spatial arrangement of tubular epithelium and blood vessels (composed of epithelium, muscle, and connective tissues) is essential for filtering, then concentrating, the urine.

Each organ is typically formed of a predominant tissue and a corresponding cell type, hence it is common to speak of heart tissue, brain tissue, etc., even when referring to an organ. It is also common to speak of tissue sections in histology, which is the study of tissues and organs.

Cells, as the building blocks of organs and tissues, are self-contained units made up primarily of water and various macromolecules. These macromolecules come in four basic types: proteins (structural molecules, enzymes, etc.), carbohydrates (sugars that are often involved in cell surface recognition), lipids (fats including those that make up cell membranes), and nucleic acids (DNA and RNA). Cells are made up of all of these macromolecules and a good deal of water and small ions (sodium, potassium, chloride, etc.) The isolation and purification of specific macromolecules from biological tissues is the traditional realm of biochemistry, though this treatment of nucleic acids is now considered the realm of molecular biology.

The localization of specific macromolecules in tissue sections can be achieved by a variety of forms of histochemistry. A tissue section is usually prepared by cutting thin sections of tissue and looking at it under a microscope, the source of illumination may be visible light (traditional light microscopy), ultraviolet light (fluorescent microscopy), or electrons (electron microscopy). If a chemical reagent is used to identify a specific substance the method is simply termed histochemistry, if a reaction involves enzymatic catalysis, the term is enzyme histochemistry. When specific antibodies are used to identify a particular antigen (or epitope) in a tissue section, the terms used are immunohistochemistry, immunocytochemistry, or immunolocalization. When specific complementary sequences of nucleic acids are used to hybridize with specific cellular nucleic acids in tissue sections, the term used is in situ hybridization histochemistry.

The macromolecules of animal tissues are typically extracted, isolated, and purified before being separated by gel electrophoresis. Once separated, these macromolecules are generally transferred and immobilized on a membrane before being probed with specific antibodies or nucleic acids in the powerful and popular techniques of Northern, Southern, and Western hybridization.

In contrast to conventional blotting, in which macromolecules are transferred to a membrane along with their relative electrophoretic positions, "tissue prints" are believed to transfer molecules (from cell juices) along with their relative tissue locations. Some components of the "cell juice" are transferred to membranes during the tissue printing of botanical tissues, however, there is no evidence yet that whole cells or groups of cells are transferred in this process.

The technique of transferring macromolecules (including proteins and nucleic acids) directly from intact tissues to nitrocellulose or other blotting membranes has been called "tissue printing" (Varner, 1992). This technique has recently gained popularity in the field of plant science in large part because of the work of Cassab and Varner (1987). Botanical tissues are particularly well-suited for tissue printing because of their characteristic structural rigidity and symmetrical tissue architecture. It is, however, possible to make tissue prints of animal tissues as well.

One step further than a tissue print is isolating individual intact cells on nitrocellulose. In Cell blotting: *Techniques for staining and microscopical examination of cells blotted on nitrocellulose paper* (Anal. Biochem. 157:331–342, 1986), Seshi taught that individual isolated cells—both normal and neoplastic cells—can be immobilized onto nitrocellulose membrane with retained cytological detail. Seshi fails, however, to realize that the cells need not be digested and isolated. All the architectural information is lost by digesting and suspending his cells. This paper discusses the use of immunological agents to detect specific molecules (in this case the Leu-4 antigen on lymphocytes and chromogranin). This study also employs specific cell adhesion molecules, in this case fibronectin, to enhance the binding of cells, in this case BHK cells, to fibronectin-treated nitrocellulose membrane during a 60 minute incubation.

In *Ion channel expression by white matter glia: The type-*1 *astrocyte* (Barres BA, Koroshetz, Chun LLY, Corey P., Neuron 5:527–544, 1990.), the authors describe what they call, "a new 'tissue print'dissociation procedure" to isolate individual cells from brain so that they could perform electrophysiology studies on them. These authors state that they wanted to use tissue printing to, "exploit this adhesion [between tissues and membranes] for cell isolation" and that they developed "an new 'tissue print'technique that produces dissociated cells. . ." (Barres et al., page 27). In some cases, brain tissue was partially digested before tissue printing onto nitrocellulose membrane; in other cases Vibrotome sections (50–100 micrometers thick) of brain tissue was printed onto nitrocellulose paper. These authors did recognize that live cells could be transferred to nitrocellulose substrata, but did not foresee the utility of the technique as a method of preserving the architectural arrangement of cells from large tissues, indeed, they developed the method for cell isolation so that they could perform electrical experiments on isolated cells with intact cell processes. In the discussion these authors state that, "The tissue print protocol is a simple variant of standard dissociation protocols." and that ". . . rather than shearing the tissue apart by passage through a syringe needle or pipette, a 'touch prep'[a technique used in clinical pathology] is prepared by gently touching the tissue to a sticky, nontoxic surface." They go on to say, "Unlike previous methods, this tissue print procedure allows isolation of viable cells still bearing processes for further study. Here we have used tissue prints for electrophysiological recording; however, we have also used the procedure for other purposes, including isolation of cells for culture, scanning electron microscopy, and immunohistochemistry." Notably, they do not mention transmission electron microscopy nor do they discuss anything about pathological tissues.

In *Simultaneous recording of [Ca2+]i increases in isolated olfactory receptor neurons retaining their original spatial relationship in intact tissue*(Hirono J, Sato T, Tonoike M, Takebayashi M., J. Neurosci. Meth. 42:185–194, 1992.) the authors teach that small slices of olfactory epithelium (i.e., smelling nerves) can be dissected and digested before "unrolling" a piece of tissue onto a glass substrate coated with the lectin Concanavalin A as an adhesive. These authors state that the "relative local arrangement between the cells" is preserved. It should be pointed out that this technique involves very small pieces of tissue with the purpose of preparing the cells for tissue culture and from the pictures shown, the tissue and organ architecture is poorly preserved.

Viles et al. describe how liver cells, isolated in primary culture and transformed by a virus, can be cultured on a semipermeable membrane. To isolate these hepatocytes, a piece of liver is digested with collagenase. Collagenase, an enzyme that breaks down the connective tissue portion of the liver, is used to disperse the hepatocytes, vascular smooth muscle cells, endothelial cells, connective tissue fibroblasts, biliary epithelium, etc. Subsequent filtration, centrifugation, washing, and culturing of this mixture of cells apparently selects for hepatocytes. These "primary" hepatocytes (i.e., cells derived directly from the liver) are grown in culture as a monolayer, exposed to the SV40 virus, and the resulting transformed (i.e., immortalized) cells are cloned (i.e., grown by the multiplication of a few stably transformed parent cells) in a specified culture medium. These transformed cells are then seeded onto a hollow fiber filter substrate that physically excludes the immortalized hepatocytes as well as the virus particles from the inner part of the fiber substrate, which is the conduit used for patient blood. Exchange of metabolites occurs across the porous fiber substrate thereby simulating the function of the liver.

Viles et al. employ a porous substrate as both a culture support to grow and maintain transformed hepatocytes, and as a semipermeable membrane to separate cultured hepatocytes from the patients blood, but the porous membrane is not used as a sampling tool.

By digesting the liver with collagenase, the in vivo/in situ organization of this organ is destroyed and with it the complex functions of the liver as an organ. Not only are the characteristic and functionally important spatial relationships among the hepatocytes destroyed, but the relationships between the hepatocytes and the other cell types are destroyed as well. Thus, while cultured hepatocytes grown in the manner described by Viles et al. may be able to subserve one or some functions of normal liver, undoubtedly many functions of the liver are lost or dramatically reduced.

To make the invention of Viles et al. practical, it is essential that hepatocytes be induced to proliferate easily in culture; this is achieved by viral transformation and selective culturing of a few clones of cells. Thus, not only is the organ architecture of the liver lost, but the phenotypic variety of hepatocytes is dramatically reduced: hepatocytes are selected primarily on their ability to be transformed and to proliferate in culture rather than on any particular functional property (such as the ability of metabolize blood-borne toxins).

Goodwin et al. simply claim that various cell types can be cultured together (cocultured) using a three-dimensional culture. The resulting co-cultures are said to be able to produce multicellular organoid tissue. While these authors place great emphasis on the ability of co-cultures to recreate some of the architectural features of an organ, there is no doubt that the resulting cultures differ vastly from the original organ (they use the terms "pseudo-glands" and "pseudo-crypts" to define the "organoid" appearance of their cultures after 138 hours of growth). If it were indeed possible to recreate the full tissue architecture of an organ, the need for organ transplantation would disappear.

Like Viles et al., Goodwin et al. obtain cells from tissues (they use an example of normal and neoplastic colon) by digesting the tissue with an enzyme that breaks down the extracellular connective tissue matrix (in this case the enzyme is trypsin). Once the tissue is digested, the dissociated cells are placed in primary culture and co-cultured on commercially available beads. It seems that the essential part of this invention are the culturing conditions (cell ratios, speed of agitation, etc.). As with Viles et al., the characteristic organization of the gastrointestinal tract is completely destroyed by trypsin digestion and the characteristic in situ organization of the colon, which is composed of epithelial cells, smooth muscle, fibroblasts, nerves, vessels, etc., is lost.

While it is laudable to try and grow "organoids" that simulate the structure and possibly some of the functions of intact organs, previous attempts have always been incomplete, including those of Viles et al. and Goodwin et al. (An analogy is trying to create diamonds from individual carbon atoms—it is more likely that you end up with coal.)

Reid et al. teach that tissue sampling is done by cutting frozen sections, which are then transferred to a nylon membrane. The microtome blade is the sampling tool. The method described by Reid et al., requires that the tissue/organ be frozen. The process of freezing is necessary to successfully section the tissue. Freezing, of course, kills all the cells, which are no longer viable and which cannot be grown in culture. Furthermore, cryosections of tissue are uniform in thickness, but are indiscriminate as to the plane of cleavage, which is wherever the microtome blade happens to cut. Thus, most cells will be cut across or through their plasma membranes.

Currently, there is no technique for transferring layers of animal tissue that retain the tissue and organ architecture and are viable when transferred.

SUMMARY OF THE INVENTION

It is the primary object of the present invention to teach a method of transferring intact, organized cells from the surfaces of biological tissues or organs to a substrate such that the cells retain the organization of the organ or tissue.

The present invention teaches that not only are certain molecules transferred to the membranes, but indeed whole cells or sheets of cells are transferred from animal tissues to these membranes. Hence the technique is more appropriately called "Tissue Transfers" or "Tissue Stripping." Animal cells are adsorbed, stripped away, and transferred from cut surfaces of fresh animal tissues to membrane substrates with high fidelity with respect to tissue and organ architecture and histomorphology.

The localization of specific macromolecules in histological sections of plant and animal tissues is usually done by conventional immunohistochemistry and in situ hybridization histochemistry. Whereas these techniques offer high spatial resolution, they are labor-intensive and require considerable proficiency. Although generally of lower spatial resolution (Cassab and Varner, 1987), tissue prints from plants yield satisfactory resolution for many purposes while offering substantial advantages in speed and simplicity during tissue preparation and hybridization. Hence, the development of the Tissue Transfer Process for animal tissues is especially useful for screening large numbers of tissues or for studying tissues of large size for the presence and localization of specific cells and macromolecules.

The method consists of transferring intact, organized cells and groups of cells from the surfaces of biological tissues or organs to a substrate. A surface of the tissue or organ is selected, in most cases, a freshly cut surface. At least one layer of intact cells is transferred by adhesion of the cells to a transfer substrate, which is a membrane, film, plate or liquid emulsion layer bound to a solid structure. The substrate is brought into contact with the selected surface and removed. A layer of cells is removed by the adhesion of the cells to the substrate and the cells retain the organization of the organ or tissue.

The Tissue Transfer Technique is a simple and efficient new method that offers several advantages over conventional techniques (of histology, cell culture, immunoblotting, and Northern blotting). It does not, however, wholly displace them. The Tissue Transfer Technique is an alternative to conventional techniques in certain circumstances where speed, large samples, access to cell surfaces, or archival storage are required at a substantial savings in cost.

The first advantage is that morphological and chemical information can be obtained and analyzed considerably faster than with conventional histological processing. Typically, the Tissue Transfer Technique can be done in less than a minute and fixation, histochemical staining, and examination can be complete in many cases in as little as 5–10 minutes. In addition, multiple samples can be obtained from the same freshly cut tissue surface thereby supplying additional and control Tissue Transfers for investigation. Due to the high fidelity of Tissue Transfer architecture, the transfers are potentially useful as a substrate for the rapid screening of tissue morphology, chemistry, enzymology, immunology, and molecular biology.

A second advantage of the Tissue Transfer process is that the surface of very large tissues (e.g. whole kidneys, large solid tumors), which otherwise would have to be cut in small pieces, can be transferred intact. This facilitates the analysis of global variation in morphology or chemistry across very large tissue samples.

A third advantage of the Tissue Transfer Technique is that more of the cell surface is exposed for study since the cells are transferred intact and their surfaces are exposed without sectioning. There is a calculated increase in cell surface area available to study of at least 50% for spheroidal cells, 150% for cuboidal cells, and even greater increases for more irregularly shaped cells. This advantage has important implications in the study and characterization of neoplastic cells, for example, where cell surface molecules are believed to play an important role in intercellular signaling and metastasis (Travis, 1993). The thinness of the tissue layer that is transferred also confers a distinct advantage for ultrastructural studies because fixation is rapid and complete.

A fourth advantage is that the Tissue Transfer Technique is that certain opaque membranes (nitrocellulose but not nylon) can be clarified by immersion in solvents of similar refractive index (e.g., xylene) and can then be mounted onto a glass slide. This feature is quite remarkable because at first glance the resulting Tissue Transfers bear a similarity to histological sections. This makes possible a direct qualitative comparison between traditional histological sections (frozen and paraffin sections) and clarified tissue prints. This development has aided immensely our understanding of what and how cellular material is transferred during the Tissue Transfer Technique and has given comfort to the pathologists who feel more at home looking at traditionally prepared tissues. The pathologists now recognize that Tissue Transfers offer information that is qualitatively different and otherwise unavailable in conventional preparations.

A fifth practical advantage of the Tissue Transfer Technique is that the transferred sheets of cells can be cultured on sterilized membranes. Since the cultured Tissue Transfers maintain the architectural features of the intact organ they offer potential as "organ monolayer cultures" that can be used to study cell and tissue physiology as well as for screening pharmacological agents and assessing tissue toxicology.

A sixth practical advantage is that the Tissue Transfer Technique is easily mastered and can be carried out by laboratory personnel trained in standard cytological techniques. Furthermore, the technique can be carried out at very low cost making it accessible technology for a variety of large and small scale applications.

BRIEF DESCRIPTION OF THE DRAWING

FIGS. 1a–d illustrate the steps involved with making a Tissue Transfer from a freshly cut piece of tissue to a membrane.

FIGS. 2a–d show organ, tissue and cellular morphology of a rabbit kidney using various Tissue Transfer preparations.

FIGS. 3a–d show immunofluorescent studies of a rabbit kidney using various Tissue Transfer preparations.

DESCRIPTION OF THE PREFERRED EMBODIMENT

Figure 4A:
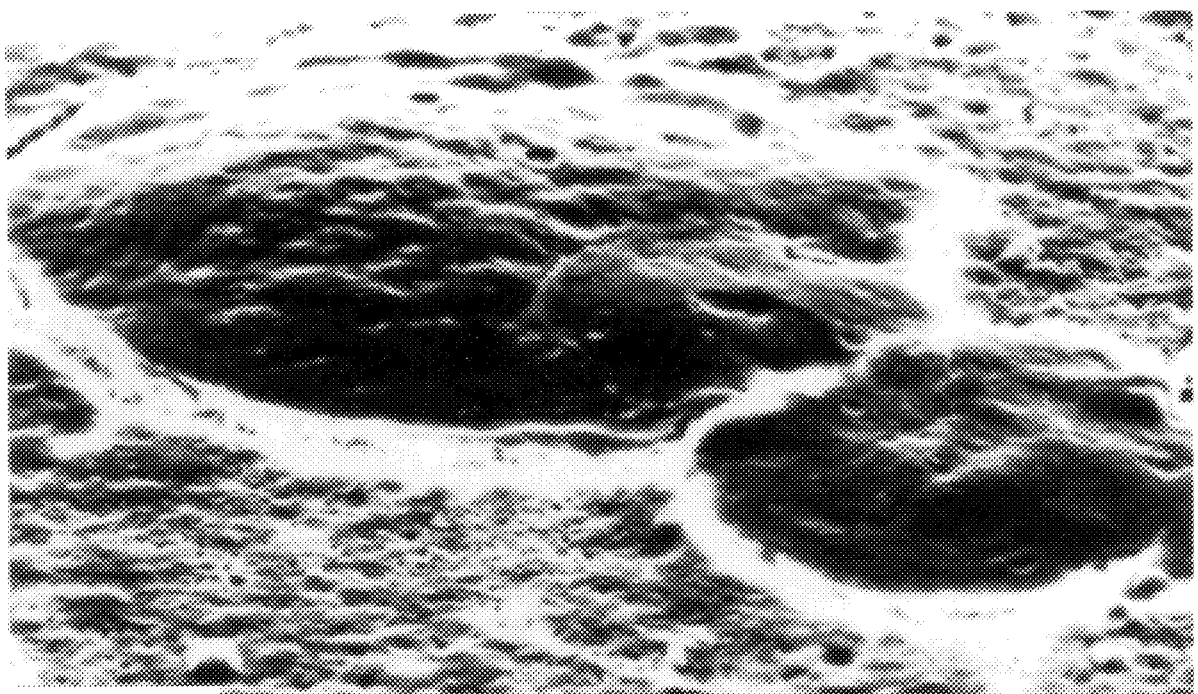
FIGS. 4a and 4b show pictures of various Tissue Transfer preparations of a rabbit kidney using a scanning electron microscope.

In the scientific literature, there have been a limited number of studies describing what has been called "tissue printing" where proteins and nucleic acids can be shown to be transferred from the cut surfaces of cells onto membranes (Reid et al., 1992). Tissue printing has been used primarily with plant tissues because their cell walls are structurally rigid facilitating printing and the symmetrical tissue architecture of plants facilitates morphological analysis. Tissue printing of plant tissues is qualitatively different than Tissue Transfers of animal tissues, since whole cells are not transferred to the substrates. The novelty of the Tissue Transfer Technique is that it allows the transfer of cells, and sheets of cells, while preserving native tissue architecture.

There are also reports that suspensions of isolated cells can be immobilized and examined cytologically on some substrates. These protocols, however, are not useful in applications where tissue and organ histomorphology are a prerequisite. The Tissue Transfer Technique differs from those in which cell suspensions are applied to filters, or cellular material is absorbed to a medium, in that the Tissue Transfer Technique provides the transfer of a tissue layer which retains high fidelity with respect to tissue and organ architecture and histomorphology. In addition, intercellular associations are maintained in the section plane.

The utility of the Tissue Transfer Technique is that cells, groups of cells, and their macromolecular constituents can be immobilized on a substrate while maintaining tissue architecture. Once immobilized, cell, tissue or organ morphology, chemistry, lectin affinity, enzyme activity, immunoreactivity, and nucleic acid composition can all be explored as a function of organ architecture and tissue location. For example, specific molecules can be detected and mapped across an organ: alkaline phosphatase enzyme activity can be localized in prostates and growth plate chondrocytes, antibody antigen complexes can be localized in the glomeruli of the renal cortex, estrogen receptor mRNA can be localized in breast carcinomas, lectins can be used to identify vascular cells in a tumor of unknown origin, antimitotic spindle antibodies can be used in identify the number and location of dividing cells in tumors, etc. Thus, the Tissue Transfer Technique has numerous potential applications in surgical pathology including the study of morphology, identification of specific cell surface receptors, diagnosis of mitotic rate/malignant grade, the identification of tumor margins, adhesion molecule density, and tumor archiving. Furthermore, using the appropriate sterilized substrates, the Tissue Transfer Technique can be carried out on surgically excised tissue as well as tissue margins remaining within the patient.

Another important advantage is that the Tissue Transfer Process exposes more cell surface area to the investigator for examination (approximately 50% more in the case of spherical cells; at least 150% more in the case of cuboidal cells). This is particularly important since it is widely believed that cell surface molecules play a central role in malignancy and the Tissue Transfer Process gives you "more to work with".

The Tissue Transfer Technique has considerable utility in industrial scientific settings and in basic science research when screening large number of tissues (e.g., to see the effect of different drugs on liver metabolism) or a large number of animals (e.g., to see the expression of a particular reporter gene in transgenic animals). In addition, the Tissue Transfer Technique is almost unique in its ability to examine the continuous distribution of a particular cell or macromolecule in very large organs (e.g., whole livers, whole brains, large solid tumors) which would otherwise have to be cut into smaller pieces for processing by traditional techniques.

It is possible to maintain Tissue Transfers in culture. Since the Tissue Transfers maintain sheets of cells with their native cell-to-cell arrangement, Tissue Transfers offer unique advantages over established (i.e. immortalized) cell lines or cells that have been digested from intact tissues and grown in culture (i.e., primary cell cultures).

FIGS. 1a–d illustrate the steps involved with making a Tissue Transfer from a freshly cut piece of tissue to a membrane. FIG. 1a shows a rabbit kidney 1 being cut with a razor blade 2. New, clean single-sided razor blades work well, however, other sharp blades, including autopsy knives, may be used. For small tissue samples razor blades and scalpels work well; for larger tissues, particularly those that arrive at the pathology bench, an autopsy knife (really just an elongated scalpel blade) works even better.

FIG. 1a shows a whole rabbit kidney 1 about to be cut in half with a razor blade 2. A large square of blotting paper 3 (e.g. Whatmann 3MM chr™ chromatography paper) is placed on the benchtop; a smaller square of membrane 4, transfer substrate, (e.g. Pall BioDyne™ membrane) is cut and positioned in the middle of the blotting membrane 3. FIG. 1b the rabbit kidney 1 cut in half exposing the newly cut kidney surface 10. Gloves are usually worn, particularly if RNA is to be preserved.

FIG. 1c shows one half of kidney 1 placed cut-surface 10 down onto the membrane 4. Depending on the size of the organ, gentle pressure may be applied. After about 30 seconds, a time that can vary, the kidney 1 is carefully lifted from the membrane 4 or the kidney-membrane complex is inverted and the membrane 4 is peeled from the surface 10 of the kidney.

FIG. 1d shows that a slight impression, some tissue fluid and some blood allows the kidney 1 to be faintly visible on the membrane 4. The same cut surface can be printed again (though the efficiency of transfer diminishes with each successive transfer) onto a fresh piece of membrane. The transfer can be fixed; e.g. neutral-buffered formalin (NBF).

The Tissue Transfer Technology has been used to transfer cells and cell layers from a variety of normal tissues (including kidney, liver, heart, muscle, ligament, lymph nodes, spleen, brain and developing bone) to a variety of different substrates. We have established that excellent cellular, tissue and organ morphology is maintained by using the Tissue Transfer Technique. As shown in the FIGS. 2–6, cells and their components can be faithfully transferred to the substrate with the preservation of the tissue architecture in the section plane. Architecture, ultrastructure, and epitopes are all preserved during the Tissue Transfer Technique.

FIGS. 2a–d show organ, tissue and cellular morphology of a rabbit kidney using various Tissue Transfer preparations. In FIG. 2a a whole rabbit kidney has been divided in half and transferred onto a nylon membrane (ICN BioTrans™) by the Tissue Transfer Technique. The resulting Tissue Transfer has been fixed with formaldehyde, stained with toluidine blue O, rinsed in ethanol, and photographed with reflected light. The overall characteristic shape of the kidney can be discerned as can the characteristic internal architecture: the outer (darker) region is the renal cortex and the inner (lighter) region is the renal medulla. The dark dots visible in the renal cortex are renal glomeruli, which are the site in the kidney where urine is filtered from the blood. The magnification in this photograph is approximately 1.8×.

FIG. 2b shows a higher magnification of kidney cortex transferred to nitrocellulose membrane (Schleicher & Schuell S&S NC™ BA85, 0.45 micrometer pore size), fixed in 3% paraformaldehyde, and stained with hematoxylin and eosin. The membrane has been clarified in xylene, the Tissue Transfer has been mounted under a coverglass on a glass microscope slide, and photographed by transmitted light. A number of glomeruli are visible as dark dots scattered among renal tubules. The approximate magnification is 16×.

FIG. 2c shows a higher magnification of a preparation similar to that in FIG. 2b. A single renal glomerulus is shown nested among kidney tubules. The approximate magnification is 150×.

For comparison with conventional histology, FIG. 2d shows a 5 micrometer-thick frozen tissue section of the same kidney used to make the Tissue Transfer in FIG. 2c, stained with hematoxylin and eosin, and photographed with transmitted light. A single renal glomerulus is shown nested among kidney tubules. The approximate magnification is 300×.

The selection of a transfer substrate is important. To date the best success has been with nitrocellulose or nylon paper. The relative efficiency with which sheets of cells are transferred by the Tissue Transfer Technique depends on the substrate: different tissues work better with different substrates. Substrates can be chosen from a variety of transfer membranes (e.g., nitrocellulose, nylon, PVDF, etc.), films, plates, and emulsion layers.

We suspect that the mechanism of the Tissue Transfer Technique depends on the formation of a vacuum created by cellular and extracellular fluid being drawn into the pores of the membrane. When this vacuum pressure exceeds the pressure needed to maintain the intercellular connections, a layer of cells is transferred to the membrane substrate. Empirically we know that pore size ranges of at least from 0.1–12 micrometers. At some point the "capillary action", i.e., water surface tension, formed by the pores might be insufficient to maintain an adequate vacuum and transfer efficiency will suffer, until at some point it no cells will be transferred.

FIGS. 3a–d show immunofluorescent studies of a rabbit kidney using various Tissue Transfer preparations. FIG. 3a shows a Tissue Transfer of rabbit kidney onto nylon membrane (Pall BioDyne™–0.45 micrometer pore size) fixed in methanol. A fluorescent histochemical counter stain for DNA (DAPI×4',6-diamino-2-phenylindole) shows the location of renal tubule cells. The approximate magnification is 625×.

FIG. 3b shows the same preparation as in FIG. 3a incubated with human anti-DNA primary antibody. Goat anti-human antibody conjugated with fluorescein was used as a secondary antibody to detect the human anti-DNA antibody, which reacts with rabbit DNA. This illustrates that nuclear epitopes are preserved during Tissue Transfers. The approximate magnification is 625×.

FIG. 3c shows a high magnification of rabbit kidney Tissue Transfer. DNA fluorescence is due to DAPI counter stain. The approximate magnification is 1500×. FIG. 3d shows the same preparation as in FIG. 3c incubated with human anti-tubulin primary antibody. Fluorescein-conjugated goat anti-human secondary antibody was used to detect the human anti-tubulin antibody. Tubulin, a polymeric cytoskeletal protein is seen in a network throughout the cytoplasm of the cell. This illustrates that cytoplasmic epitopes are preserved by the Tissue Transfer Technique. The approximate magnification is 1500×.

Figure 4B:
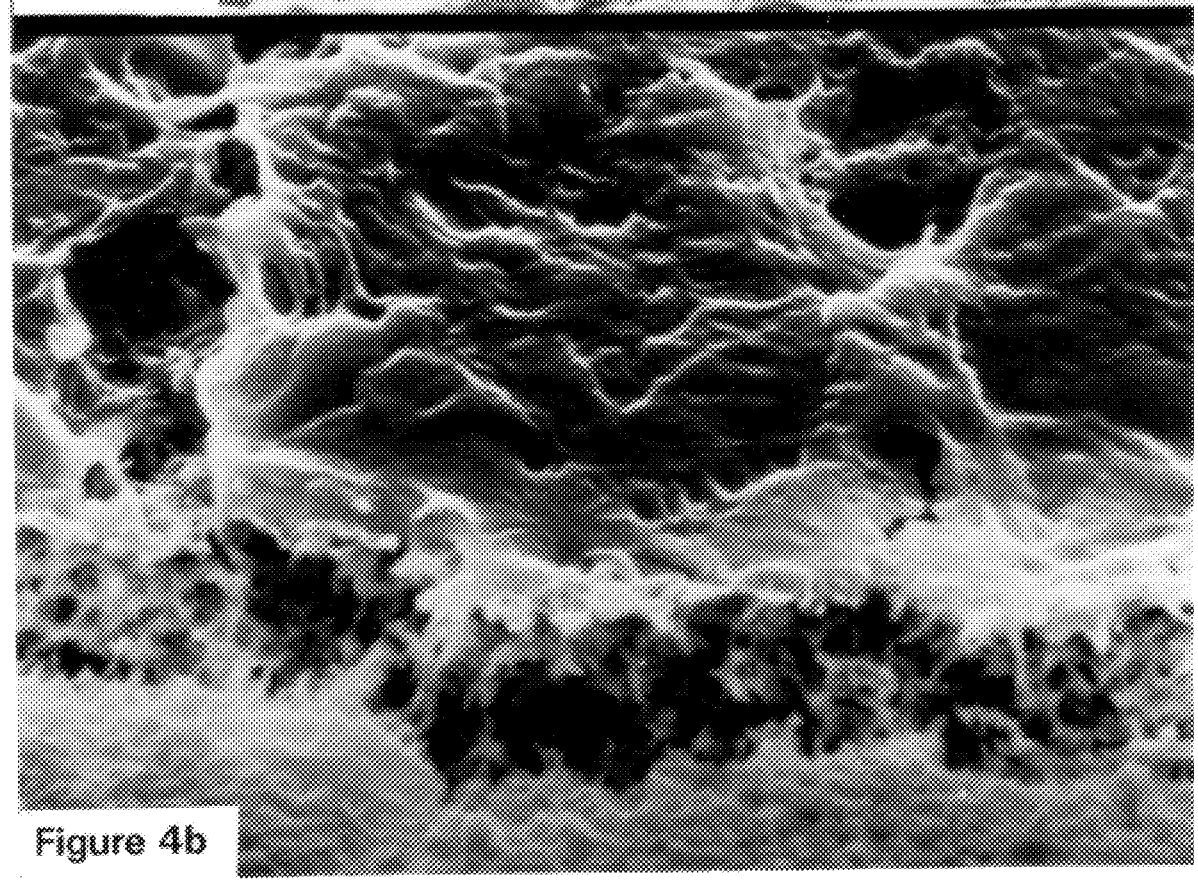

FIGS. 4a and 4b show pictures of various Tissue Transfer preparations of a rabbit kidney using a scanning electron microscope. FIG. 4a shows a Tissue Transfer of rabbit kidney onto nylon membrane (BioDyne™), fixed in acetone, sputter-coated with gold-palladium, and examined by scanning electron microscopy. The two disc-shaped objects are renal glomeruli. This preparation shows the retention of tissue architecture and the three-dimensional features of glomeruli in Tissue Transfers. The approximate magnification is 1300×. FIG. 4b shows a higher magnification of the same preparation shown in (a). This photomicrograph was taken at the border between the membrane (below) and the larger renal glomerulus (above). The approximate magnification is 2600×.

Figure 5A:
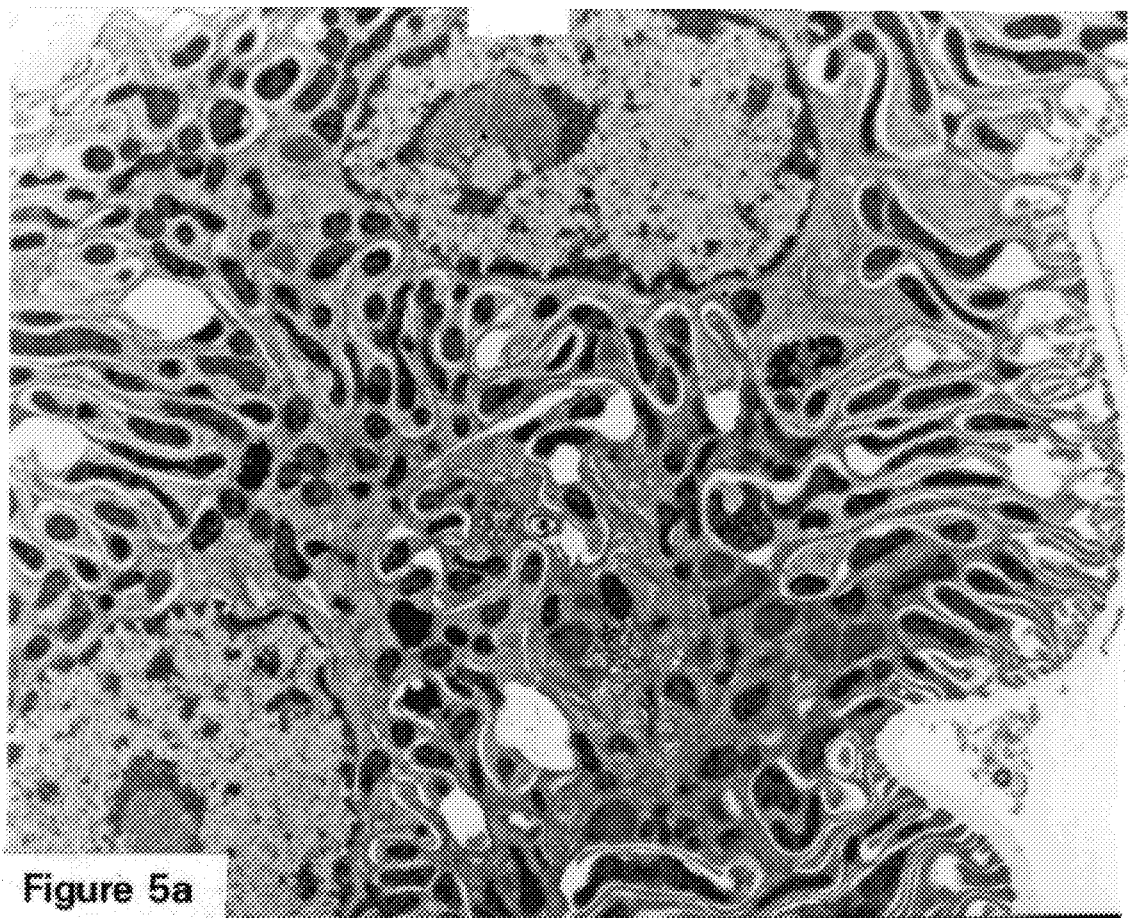
FIGS. 5a and 5b show pictures of various Tissue Transfer preparations of a rabbit renal tubule using a transmission electron microscope.
Figure 5B:
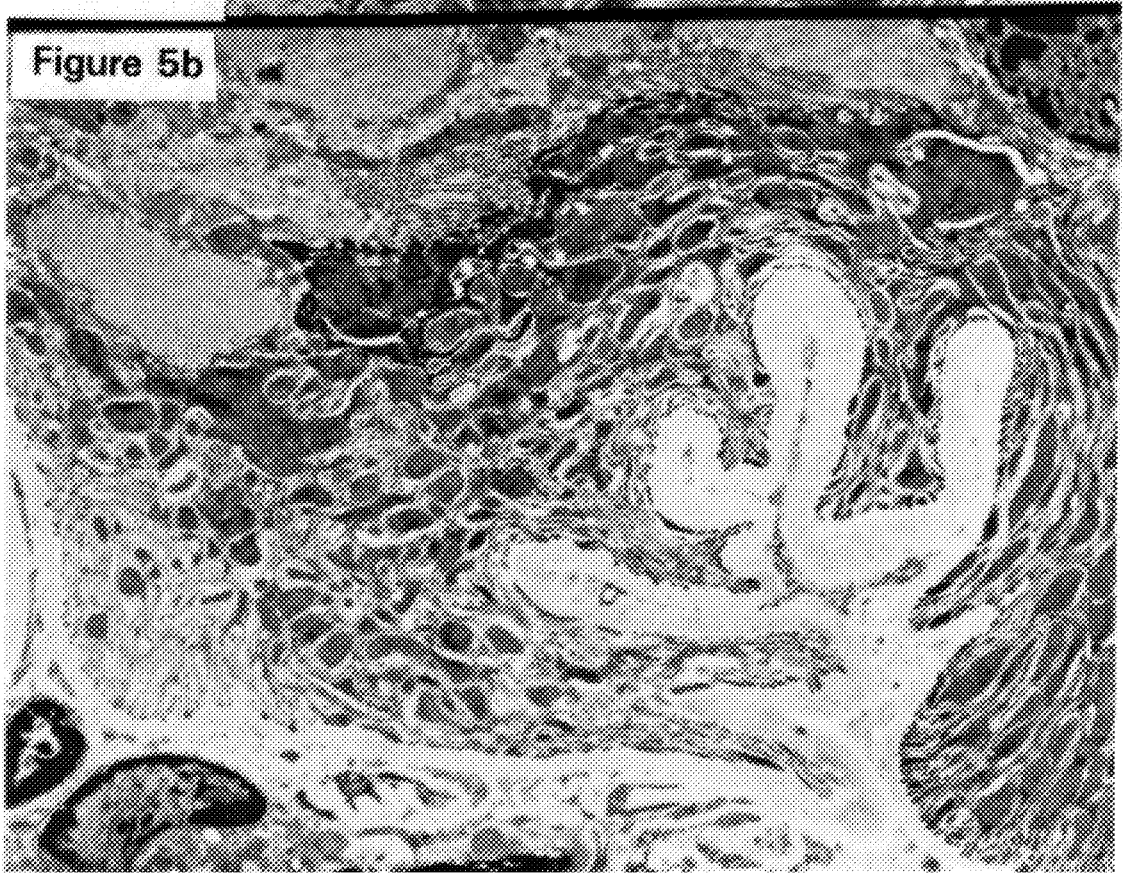

FIGS. 5a and 5b show pictures of various Tissue Transfer preparations of a rabbit renal tubule using a transmission electron microscope. FIG. 5a shows and electron micrograph of Tissue Transfer of rabbit renal tubule fixed in glutaraldehyde, post-fixed in osmium tetroxide, and stained with lead citrate and uranyl acetate. Two nuclei can be seen as well as numerous mitochondria. The extensive infolding of the cytoplasmic membrane is characteristic of these cells. The basement membrane of the tubule is on the right; membrane off to the left. This micrograph illustrates the excellent morphological preservation of all the cellular organelles including membranes that is possible in Tissue Transfers. The approximate magnification is 10,000×.

FIG. 5b shows an electron micrograph of Tissue Transfer of rabbit renal tubule. The surface of the nylon membrane is visible as a dark line along the bottom. As in FIG. 5a the ultrastructural features of the cells and organelles are well preserved. An interesting feature of this micrograph is the preservation of a nucleus that appears to have been partially sucked down through a pore in the membrane (lower left). This type of morphological feature suggests that the mechanism whereby cells and tissues are adsorbed onto the surface of the membrane involves capillary action. (Alternatively, it is possible that even gentle pressure "sieves" organelles.) The approximate magnification is 12,500×.

Figure 6A:
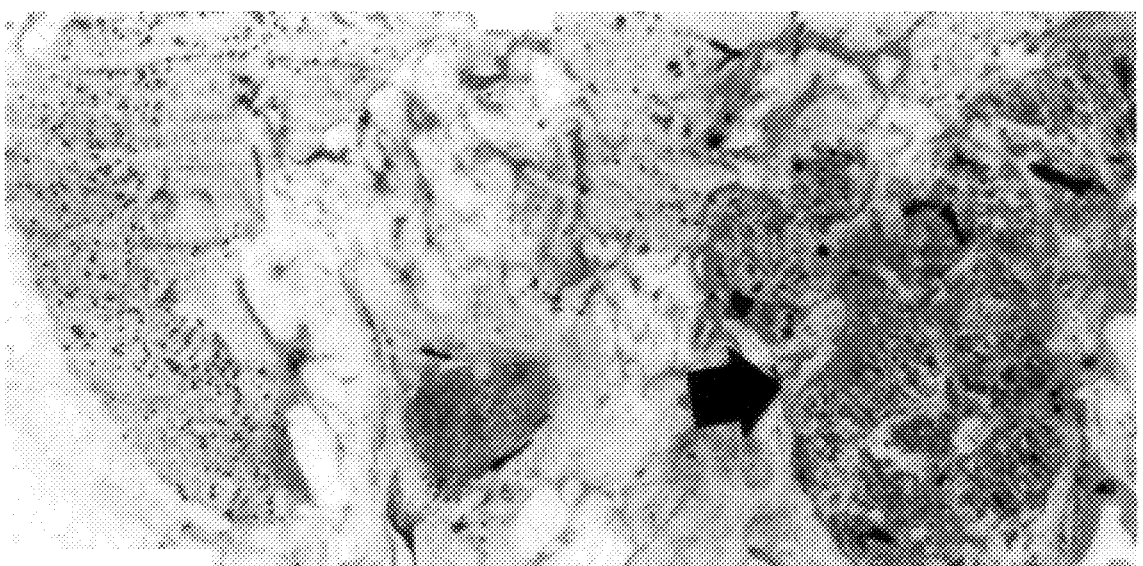
FIGS. 6a and 6b show pathological morphology studies of a human kidney using various Tissue Transfer preparation.
Figure 6B:
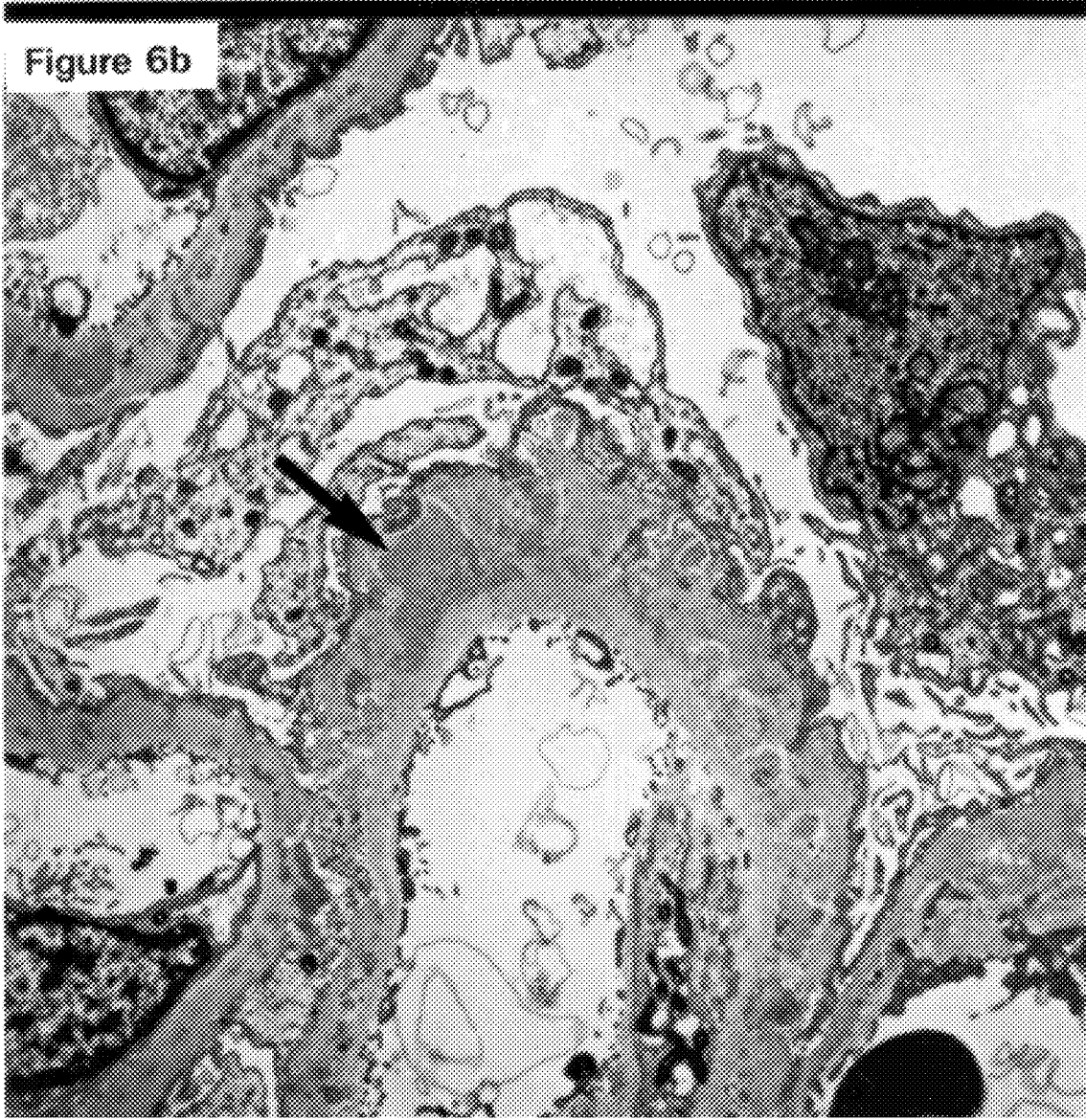

FIGS. 6a and 6b show pathological morphology studies of a human kidney using various Tissue Transfer preparations. FIG. 6a shows a very low magnification (approximately 1.25×) of a Tissue Transfer on nitrocellulose of a human kidney. The characteristic outline of the kidney is visible in this Tissue Transfer which has been stained with hematoxylin and eosin and mounted on a glass slide. The glomeruli are clearly visible as dark dots in the renal cortex and a mass of malignant cells (a renal cell carcinoma) is clearly visible to the right of the arrow. The margins of the tumor are clearly visible macroscopically as well as microscopically. This illustrates the utility of Tissue Transfers to identify tumor margins in large tissues.

FIG. 6b shows an electron micrograph of Tissue Transfer of a human renal glomerulus that has been retrieved from a renal biopsy. The definitive diagnosis of lupus nephritis was made on this Tissue Transfer; the arrow points out the characteristic electron-dense immune complex deposits in the glomerular basement membrane. The preservation of ultrastructure is excellent. The approximate magnification is 7,500×.

While the primary utility of the Tissue Transfer Technique is the transfer of large pieces of tissue while retaining tissue architecture, the technique of isolating cells on a transfer membrane can also be used as a method for harvesting material routinely lost during biopsy sampling. It is possible to use the isolation procedure to harvest large and small fragments of biopsy material that are very difficult to collect by conventional procedures. This recovered material has been studied by light and electron microscopy. This material retains its morphological and chemical characteristics and can be used in diagnostic studies along with material harvested by conventional means. The transfer of biopsy material to a transfer membrane may help save glomeruli that are lost during renal biopsy. This may make it possible to minimize patient morbidity (fewer or extra biopsies) and to maximize the material available to pathological diagnosis hence increasing the accuracy of the diagnosis. The Tissue Transfer Technique can also be used to study renal and breast tumors.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of transferring a layer of organized cells with intact cell membranes from animal tissue or organ to a porous membrane substrate wherein said layer of organized cells has the indentifiable cellular organization of said animal tissue or organ, said method comprising the steps of a) selecting a layer of cells from animal tissue or organ;

b) contacting said porous membrane substrate with said layer of cells; and c) removing said substrate from said animal tissue or organ such that said layer of cells is transferred to said membrane and retain said identifiable cellular organization of said animal tissue or organ.

2. The method of claim 1 wherein said layer of cells is exposed by cutting said animal tissue or organ to expose a smooth surface that was not exposed prior to cutting.

3. The method of claim 1 wherein said cells transferred to said porous membrane substrate are preserved by air drying, freeze drying or chemical fixation.

* * * * *